(12) United States Patent
D'Addario et al.

(10) Patent No.: US 8,535,397 B2
(45) Date of Patent: Sep. 17, 2013

(54) PROCESS FOR THE EXTRACTION OF FATTY ACIDS FROM ALGAL BIOMASS

(75) Inventors: Ezio Nicola D'Addario, Monterotondo (IT); Federico Capuano, Rieti (IT); Edoardo D'Angeli, Rome (IT); Roberto Medici, Monterotondo (IT)

(73) Assignee: ENI S.p.A., Rome (IT)

( * ) Notice: Subject to any disclaimer, the term of this patent is extended or adjusted under 35 U.S.C. 154(b) by 271 days.

(21) Appl. No.: 13/001,980

(22) PCT Filed: Jun. 19, 2009

(86) PCT No.: PCT/EP2009/004617
§ 371 (c)(1),
(2), (4) Date: Mar. 30, 2011

(87) PCT Pub. No.: WO2010/000416
PCT Pub. Date: Jan. 7, 2010

(65) Prior Publication Data
US 2011/0179699 A1    Jul. 28, 2011

(30) Foreign Application Priority Data
Jun. 30, 2008 (IT) .............................. MI2008A1203

(51) Int. Cl.
*C10L 1/18* (2006.01)
(52) U.S. Cl.
USPC ............... 44/385; 44/388; 435/134; 554/174; 554/207
(58) Field of Classification Search
USPC .................................................. 44/385, 388
See application file for complete search history.

(56) References Cited

U.S. PATENT DOCUMENTS
2009/0071064 A1* 3/2009 Machacek et al. .............. 44/308

OTHER PUBLICATIONS
U.S. Appl. No. 13/147,928, filed Sep. 28, 2011, D'Addario et al.
Pyle, D., et al., "Production of Omega-3 Polyunsaturated Fatty Acid from Biodiesel-Waste Glycerol by Microalgal Fermentation," American Society of Agricultural and Biological Engineers, Paper No. 077028, pp. 6436-6445, (Jun. 17, 2007) XP 008107255.
Belarbi, E.-H., et al., "A process for high yield and scaleable recovery of high purity eicosapentaenoic acid esters from microalgae and fish oil," Process Biochemistry, vol. 35, pp. 951-969, (2000) XP002543969.
Cranwell, P.A., et al., "Decomposition of aquatic biota and sediment formation: bound lipids in algal detritus and lake sediments," Freshwater Biology, vol. 9, pp. 305-313, (1979) XP 002543970.
Kim, M.K., et al., "Enhanced production of *Scenedesmus* spp. (green microalgae) using a new medium containing fermented swine wastewater," Bioresource Technology, vol. 98, pp. 2220-2228, (Nov. 1, 2006) XP 00253971.
International Search Report issued Sep. 15, 2009 in PCT/EP09/004617 filed Jun. 19, 2009.

* cited by examiner

*Primary Examiner* — Cephia D Toomer
(74) *Attorney, Agent, or Firm* — Oblon, Spivak, McClelland, Maier & Neustadt, L.L.P.

(57) ABSTRACT

Process for the extraction of fatty acids from algal biomass comprising: producing an aqueous suspension of algal biomass; subjecting the aqueous suspension of algal biomass to acid hydrolysis and extraction by the addition of at least one non-polar organic solvent and at least one inorganic acid to said aqueous suspension of algal biomass, so as to obtain the following three phases: (i) a semisolid phase comprising a slurry of the algal biomass; (ii) an aqueous phase comprising inorganic compounds and hydrophilic organic compounds; (iii) an organic phase comprising fatty acids and hydrophobic organic compounds other than said fatty acids.

32 Claims, 1 Drawing Sheet

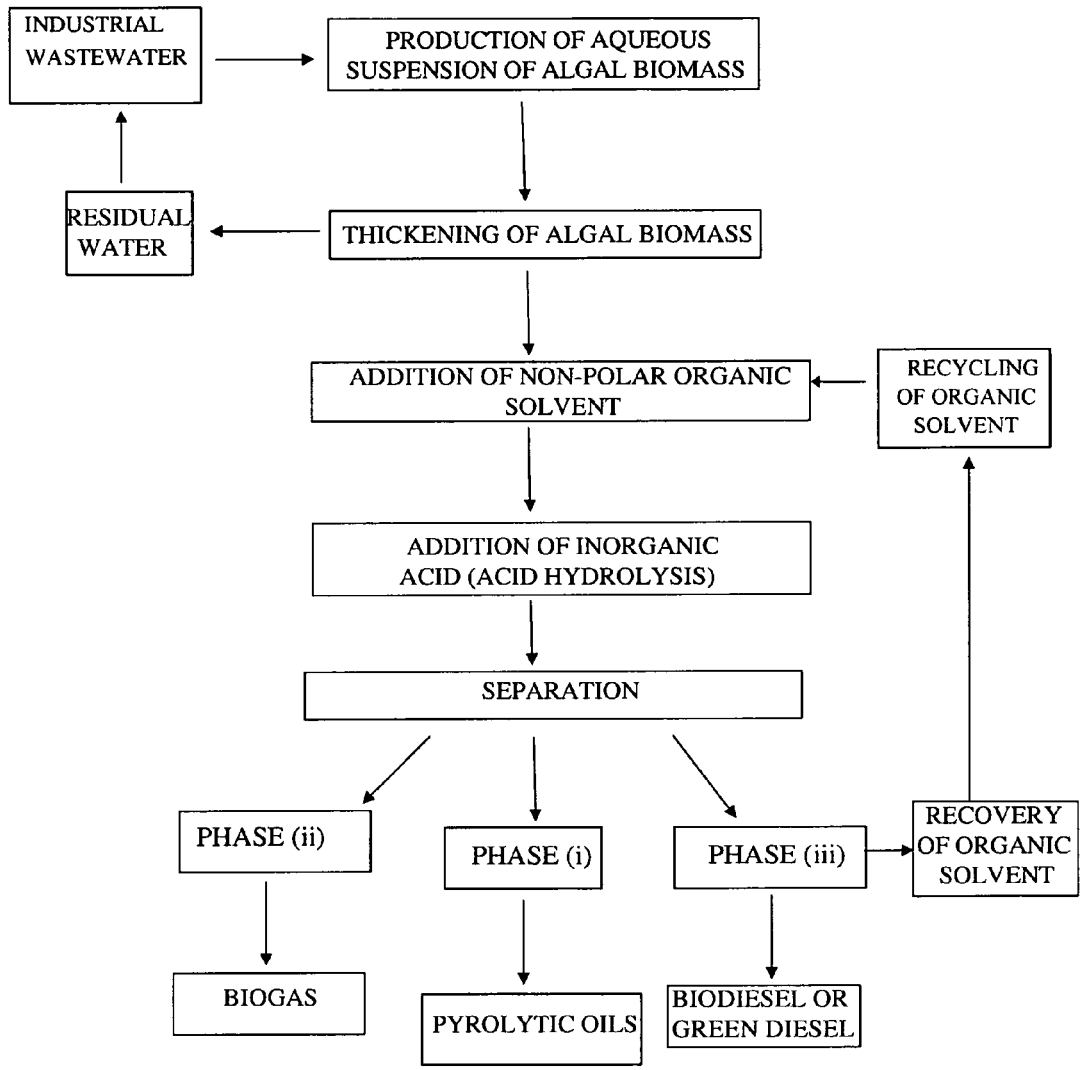

PROCESS FOR THE EXTRACTION OF FATTY ACIDS FROM ALGAL BIOMASS

This application is a National Stage of PCT/EP09/004617 filed Jun. 19, 2009 and claims the benefit of Italian application MI2008A 001203 filed Jun. 30, 2008.

The present invention relates to a process for the extraction of fatty acids from algal biomass.

More specifically, the present invention relates to a process for the extraction of fatty acids from algal biomass comprising the treatment of an aqueous suspension of algal biomass with at least one organic non-polar solvent and at least one inorganic acid.

Algae, in particular, microalgae, are currently cultivated for the production of valuable compounds such as, for example, poly-unsaturated fatty acids [for example, eicosapentaenoic acid (EPA), docosahexaenoic acid (DHA), and the like], vitamins (for example, β-carotene, and the like) and gelifying agents, which are included in the nutritional, pharmaceutical and cosmetic fields.

The cultivation of microalgae for the above sectors is characterized by rather limited production capacities (in the order of hundreds-thousands tons per year) with a high added value of the compounds obtained (hundreds-thousands dollars per kilogram). This is the reason why complex and expensive production systems, particularly extraction and purification systems, which must satisfy the strict regulations of the sanitary and nutritional type, typical of the above-mentioned fields, can be tolerated.

The shift from the above-mentioned fields of the traditional use of microalgae, to the environmental/energy field, requires the development of technologies which lead to strong increases in the production capacity (from hundreds-thousands tons per year to millions tons per year) and a strong reduction in the production costs due to the limited added value of the products destined for the environmental/energy field (hundreds-thousands dollars per ton).

Processes relating to the extraction of compounds from algal biomasses are described in the art.

The U.S. Pat. No. 4,341,038, for example, describes a process for the recovery of oily products from algae comprising: (a) growing unicellular halophilic algae, without a cellular wall, in a saline solution; (b) collecting these algae in order to obtain a slurry based on algae and saline water; (c) extracting the oily products from said slurry using a solvent for said products; (d) recovering said oily products and residual algae. Said oily products can be used as energy sources, in particular fuel, or as source of other products such as, for example, fertilizers, or animal nutrition.

The U.S. Pat. No. 5,338,673 describes a process for the selective production of poly-unsaturated fatty acids from a culture of microalgae of the species *Porphyridium cruentum*, as well as a process for their extraction. In particular, the extraction process includes: concentrating the algal biomass; subjecting said concentrated algal biomass to cell lysis, preferably by means of mechanical homogenization; separating the liquid phase from the solid phase, said solid phase containing said poly-unsaturated fatty acids; extracting said poly-unsaturated fatty acids using an organic solvent such as, for example, hexane or chloroform; evaporating said organic solvent in order to obtain said poly-unsaturated fatty acids.

Said poly-unsaturated fatty acids, such as, for example, eicosapentaenoic acid (EPA), docosahexaenoic acid (DHA), arachidonic acid, are particularly used in the pharmaceutical sector.

The U.S. Pat. No. 5,539,133 describes a method for obtaining lipids with a high amount of poly-unsaturated fatty acids having from 20 to 22 carbon atoms, through the extraction from a raw material of an animal or vegetable origin, said raw material having a water content of from 5% by weight to 50% by weight and a particle-size of from 0.01 mm to 50 mm, said extraction being carried out using an organic solvent, preferably miscible with water (e.g., ethanol) or through liquefied compressed gas (e.g., carbon dioxide, propane, or blends thereof). As raw material which can be used for this purpose, unicellular algae (microalgae), or macroalgae belonging to the family of red, brown o green algae, are also indicated. Said polyunsaturated fatty acids such as, for example, docosahexaenoic acid (DHA), arachidonic acid, are particularly used in the food industry.

The U.S. Pat. No. 6,166,231 describes a process for separating lipids, in particular food oils, from a material of a biological origin (e.g., algae, yeasts or bacteria) which comprises: (a) contacting a solvent (e.g., hexane, or various petroleum ethers) with an aqueous suspension of the material of biological origin containing the lipids in countercurrent, said solvent being essentially immiscible with water; (b) collecting the solvent, said solvent containing the lipids extracted from said aqueous suspension of the material of a biological origin; and (c) separating the lipids from said solvent.

Said aqueous suspension of the material of a biological origin is preferably subjected to centrifugation in order to reach a concentration of solid substance in the suspension not higher than 50% and, subsequently, to cell lysis by means, for example, of mechanical homogenization. An improved extraction of the lipids can be obtained through an increase in the pH, preferably between 5 and 10, of said material of a biological origin through methods known in the art, such as, for example, by the addition of a caustic solution (e.g., potassium hydroxide or sodium hydroxide). The increase in the pH also prevents the formation of emulsions between the material of a biological origin and the solvent.

Miao X. et al. describe the production of biodiesel from algae in the following article: "Biodiesel production from heterotrophic microalgal oil", published in "Bioresource Technology" 97 (2006), pg. 841-846. In said article, algae of the species *Chorella protothecoides*, grown heterotrophically, are dried and subsequently pulverized in a mortar and subjected to extraction with hexane in order to extract the oil. The extracted oil is subsequently subjected to acid transesterification in the presence of methanol and sulfuric acid as transesterification catalyst, in order to obtain biodiesel.

The production of biodiesel from algae is also described by Hossain S. et. al. in the following article: "Biodiesel Fuel Production from Algae as Renewable Energy", published in "American Journal of Biochemistry and Biotechnology" 4 (3) (2008), pg. 250-254. In said article, algae of the species *Oedogonium* and *Spirogyra*, after being ground and pestled as much as possible, are dried in a thermostatic oven at 80° C., for 20 minutes to eliminate the water. Subsequently, a solution of hexane and ether is mixed with the dried algae to extract the oil. The extracted oil is recovered by means of vacuum evaporation from said hexane and ether solution. The transesterification reaction of the oil thus obtained, for the purpose of obtaining biodiesel, is carried out in the presence of a blend of sodium hydroxide as transesterification catalyst, and methanol (basic transesterification).

The above processes, however, can have various critical points, such as, for example:
  cell lysis of the biomass normally effected by mechanical homogenization, grinding or pulverization, so as to free the intra- and endo-cellular lipid fractions and improve the contact with the solvent;

drying of the biomass normally effected by means of costly techniques, such as, for example, spray-drying or lyophilization, an operation which also requires particular attention to the temperature used during the drying which must be kept within a certain range so as not to jeopardize the quality of the compounds (e.g. lipids) to be extracted;

difficult separation of the aqueous phase from the solvent phase containing the lipid fractions, an operation which can be particularly difficult due to the formation of emulsions.

The Applicant has now found that the extraction of fatty acids from algal biomass can be advantageously carried out by means of a process comprising the treatment of an aqueous suspension of algal biomass with at least one non-polar organic solvent and at lest one inorganic acid. Said process allows both the acid hydrolysis of the lipid fraction present in the algal biomass, in order to obtain fatty acids, and the contemporaneous extraction of said fatty acids, to be effected. In particular, said process allows the following three phases to be obtained, with no further interventions: (i) a semisolid phase comprising a slurry of the algal biomass; (ii) an aqueous phase comprising inorganic compounds and hydrophilic organic compounds; (iii) an organic phase comprising fatty acids and hydrophobic organic compounds different from said fatty acids.

An object of the present invention therefore relates to a process for the extraction of fatty acids from algal biomass, comprising:

producing an aqueous suspension of algal biomass;

subjecting the aqueous suspension of algal biomass to acid hydrolysis and extraction by the addition of at least one non-polar organic solvent and at least one inorganic acid to said aqueous suspension of algal biomass, in order to obtain the following three phases:
  (i) a semisolid phase comprising a slurry of the algal biomass;
  (ii) an aqueous phase comprising inorganic compounds and hydrophilic organic compounds;
  (iii) an organic phase comprising fatty acids and hydrophobic organic compounds other than said fatty acids.

The lipid fraction present in the algal biomass deriving from the cultivation of microalgae, generally comprises various groups of lipid molecules, such as, for example: glycerides, for example, mono-, di-, tri-acylglycerides (which contain fatty acids); waxes (which contain fatty acids plus alcohols and fatty acids plus sterols); hydrocarbons; free fatty acids; sterols; phospholipids, such as, for example, diacylphosphoglycerides, alkyl-acyl-phospholipids, alkenyl-acyl-phosphoglycerides (which contain fatty acids plus a phosphoric group), sphingophospho-lipids (which contain fatty acids plus a phosphoric group and nitrogenated base); glycolipids (which contain fatty acids plus carbohydrates and nitrogenated base); aminolipids (which contain fatty acids and nitrogenated base). In addition to these lipid molecules, other hydrophobic organic compounds, such as, for example, chlorophylls, carotenoids, terpenes; tocopherols, are generally present in said algal biomass.

The above-mentioned lipid fraction and said other hydrophobic organic compounds are normally extracted by means of solvents, operating according to processes known in the art, such as, for example, those described in the documents reported above.

As mentioned above, the addition of at least one non-polar organic solvent and at least one inorganic acid to the above-mentioned aqueous suspension of algal biomass, according to the process object of the present invention, allows both the acid hydrolysis of said lipid fraction obtaining fatty acids, and the extraction of said fatty acids, to be simultaneously effected. Furthermore, the process object of the present invention allows to obtain, in addition to the above-mentioned fatty acids, hydrophilic alcohols, such as, for example, glycerine from triglycerides, methyl alcohol from chlorophylls; long-chain hydrophobic alcohols, such as, for example, phytol from chlorophylls; hydrophobic organic compounds which, during the acid hydrolysis, are only partially hydrolyzed or are not hydrolyzed. At the end of the hydrolysis and extraction, the compounds thus obtained are divided, as a result of their different characteristics, between the organic phase (hydrophobic) and the aqueous phase (hydrophilic).

It has been verified that the acid hydrolysis of the aqueous suspension of the algal biomass, allows the fatty acids which are released to be instantaneously solubilized in the solvent, thus avoiding the formation of emulsions and consequently favouring their recovery, for example, by solvent evaporation.

The aqueous phase (ii) preferably comprises inorganic compounds (for example, part of the inorganic acid used for the acid hydrolysis; nitrogen salts and potassium salts deriving from the cultivation of algae) and hydrophilic organic compounds (for example, glycerine; methyl alcohol; amino acids and polypeptides deriving from the hydrolysis of the protein substances present in the algal biomass). Said hydrophilic organic compounds are generally present in a small amount.

The organic phase (iii) preferably comprises, in addition to fatty acids, hydrophobic organic compounds different from fatty acids such as, for example, phytol and other long-chain hydrophobic alcohols, chlorophyll, carotenoids.

The aqueous suspension of algal biomass preferably derives from the cultivation of algae, preferably unicellular (microalgae), effected on wastewaters coming from industrial wastewaters. In this case, the algal cultivation metabolizes the substances containing nitrogen and/or phosphorous contained therein contributing to their purification. The $CO_2$ contained in industrial combustion gases (refinery plants, thermoelectric stations, hydrogen generation plants, etc.) can be used as the $CO_2$ necessary for algal growth.

The aqueous suspension of algal biomass is preferably subjected to thickening to obtain a higher concentration of dry substance in said algal biomass. Said thickening can be effected by means of various processes, such as, for example:

gravitational separation in sedimentators usually used in water treatment plants;

vacuum filtration;

treatment by means of belt filter presses.

The sedimentation of algal strains of fresh water such as, for example, the strain *Scenedesmus* sp, can be facilitated by the use of cationic polyelectrolytes (e.g. polyacrylamides) used in amounts of 2 ppm-5 ppm (transition of the algal concentration from 0.4 g/l to 40-50 g/l in a few hours).

For the purposes of the present description and of the claims which follow, the definition of the numerical ranges always comprises the extremes, unless otherwise specified.

According to one preferred embodiment of the present invention, the aqueous suspension of algal biomass has a concentration of dry substance ranging from 3% by weight to 40% by weight, more preferably from 5% by weight to 35% by weight, with respect to the total weight of the aqueous suspension of algal biomass.

According to a preferred embodiment of the present invention, the non-polar organic solvent can be selected from aliphatic hydrocarbons, such as, for example, hexane, n-octane; aromatic hydrocarbons such as, for example, xylene isomers; refinery cuts comprising blends of said aliphatic and/or aromatic hydrocarbons, said refinery cuts preferably having a boiling point ranging from 60° C. to 160° C.; petroleum ethers; or blends thereof. Hexane, n-octane or blends thereof are preferred.

Other solvents, such as, for example, ethers, ketones, chlorinated hydrocarbons or blends thereof are not excluded from the present invention, on the condition that they are immiscible with water.

In accordance with a preferred embodiment of the present invention, the ratio between the concentration of dry substance in the algal biomass and the volume of non-polar organic solvent ranges from 1:1 to 1:80, preferably from 1:3 to 1:70.

In accordance with one preferred embodiment of the present invention, the inorganic acid can be selected from sulfuric acid, hydrochloric acid, phosphoric acid, nitric acid, or blends thereof. Sulfuric acid, hydrochloric acid, phosphoric acid, or their blends, are preferred.

In accordance with one preferred embodiment of the present invention, the ratio between the concentration of dry substance in the algal biomass and the volume of inorganic acid ranges from 1:0.01 to 1:5, preferably from 1:0.02 to 1:3.

In accordance with one preferred embodiment of the present invention, the acid hydrolysis and the extraction are carried out, at atmospheric pressure, at the boiling point of the solvent when said temperature is lower than 100° C., or at 100° C. when the boiling point of the solvent is higher than 100° C. The acid hydrolysis and the extraction are preferably carried out at atmospheric pressure, at 100° C.

In accordance with a further embodiment of the present invention, the acid hydrolysis and extraction are effected at a temperature of 100° C., at the equilibrium pressure of the solvent at this temperature.

In accordance with one preferred embodiment of the present invention, the acid hydrolysis and extraction are carried out at a pH value ranging from 0.5 to 3. The acid hydrolysis and extraction are preferably carried out at a pH value of 2.

In accordance with one preferred embodiment of the present invention, the acid hydrolysis and extraction are carried out for a period ranging from 1 hour to 3 hours. The acid hydrolysis and extraction are preferably carried out for a period of 2 hours.

In accordance with one preferred embodiment of the present invention, the non-polar organic solvent and the inorganic acid are added contemporaneously to the algal biomass.

In accordance with a further embodiment of the present invention, the non-polar organic solvent is added to the algal biomass before the inorganic acid.

In accordance with a further embodiment of the present invention, the non-polar organic solvent is added to the algal biomass after the inorganic acid.

At the end of the hydrolysis and extraction, the following three phases are obtained (i)-(iii) which separate by gravity. Said three phases (i)-(iii) are subsequently recovered and subjected to treatment known in the art in order to obtain the compounds of interest.

It should be noted that the three phases (i)-(iii) easily separate by gravity without the necessity for any particular separation treatment.

Preferably, the semisolid phase (i) comprising a slurry of the algal biomass, after the removal of the residual water by means of processes known in the art, for example, through decantation, is subjected to pyrolysis in order to obtain pyrolytic oils.

Preferably, the aqueous phase (ii) comprising inorganic compounds and hydrophilic organic compounds, is subjected to anaerobic digestion by means of microorganisms in the absence of oxygen in order to obtain biogas (methane, in a percentage of 500-70%, carbon dioxide and other reaction by-products).

Alternatively, phase (i) and phase (ii) can be mixed and subsequently subjected to anaerobic digestion by means of microorganisms, in the absence of oxygen, to obtain biogas.

It should be noted that in the production of biogas, it is preferable not to use sulfuric acid as non-polar organic solvent as it could negatively interfere in the production of the same biogas. Competition phenomena could arise, for example, between methanogenic and sulfur-reducing bacterial florae due to the presence of significant concentrations of sulfate, or relevant amounts of sulfuric acid could develop in the biogas produced. In the case of the production of biogas, it is preferable to use hydrochloric acid as non-polar organic solvent.

The organic phase (iii) comprising fatty acids and other hydrophobic organic compounds different from said fatty acids, is preferably subjected to an evaporation step in order to recover the non-polar organic solvent which is recycled to the process, the fatty acids and the other hydrophobic organic compounds different from said fatty acids. After evaporation, said organic phase (iii) is esterified in the presence of an alcohol having from 1 to 4 carbon atoms, preferably methanol, ethanol, and an acid or basic catalyst, to produce glycerol and alkyl esters, in particular methyl esters or ethyl esters (biodiesel).

Alternatively, after evaporation, said organic phase (iii) can be subjected to hydrogenation/deoxygenation in the presence of hydrogen and a catalyst with the aim of producing green diesel. Hydrogenation/deoxygenation processes are known in the art and described, for example, in European Patent Application EP 1,728,844.

Depending on the specific use of the biodiesel or green diesel produced as described above and which can be used as such or in a blend with other fuels for motor vehicles, the hydrophobic organic compounds different from said fatty acids which, contrary to said fatty acids, are not esterified or hydrogenated/deoxygenated, can remain in said biodiesel or green diesel, or can be removed using techniques known in the art, such as, for example, treatment with adsorbing solid materials (for example, silica gel, or other porous polar materials) or thermal treatment.

Alternatively, the organic phase (iii) comprising fatty acids and other hydrophobic organic compounds different from said fatty acids, can be directly to esterification or subjected hydrogenation/deoxygenation. In this case, the evaporation step of the non-polar organic solvent is avoided.

The present invention is now illustrated in greater detail by means of an illustrative form with reference to FIG. 1 below reported.

According to a typical embodiment of the process of the present invention, the aqueous suspension of the algal biomass is produced through algae cultivation, preferably microalgae effected on wastewaters from industrial wastewaters. The production of microalgae, for example, can be suitably carried out by combining cultivation systems such as photoreactors and open ponds.

The aqueous suspension of algal biomass thus obtained is thickened by gravitational separation.

The residual water with a reduced content of nitrogenated and/or phosphoric polluting substances can be discharged directly, or subjected to finishing purification treatment before being discharged, to be able to comply with the law requirements (not shown in FIG. 1).

If the water available for the algae cultivation is not sufficient, the water released from the thickening of the algal biomass can be recycled to a large extent and reused in the process as industrial wastewater (as shown in FIG. 1).

The thickened algal biomass is preferably fed to a reactor equipped with a reflux cooler.

The following products are then fed to said reactor:
- an aqueous suspension of algal biomass having a variable content of dry substance, preferably from 5% by weight to 40% by weight with respect to the total weight of the aqueous suspension of algal biomass;
- a non-polar organic solvent, preferably hexane or n-octane;
- an inorganic acid, preferably sulfuric acid or hydrochloric acid, until a pH of about 2 is obtained.

Said reactor, maintained at atmospheric pressure, is heated to the boiling point of the solvent when said temperature is lower than 100° C., or to 100° C. if said temperature is higher than 100° C. Said temperature is kept constant by means of the reactor cooler which condenses the water which evaporates.

The formation of fatty acids, due to the acid hydrolysis to which the algal biomass is subjected, is monitored by means of gas-chromatographic analysis of the solvent.

When the hydrolysis and the extraction have been concluded (verified by means of gas chromatographic analysis: further details relating to said analysis are provided in the examples which follow), the three phases (i), (ii) and (iii) separate by gravity. Said three phases (i), (ii) and (iii) are preferably subjected to the treatment described above in order to obtain: pyrolytic oils, biodiesel or green diesel, biogas.

Some illustrative and non-limiting examples are provided for a better understanding of the present invention and for its embodiment.

EXAMPLE 1

Preparation of the Algal Biomass

In the following examples 2-6 the algal strain *Scenedesmus* sp., of the internal collection, which normally grows in fresh water, was used. The cultivation process adopted is described hereunder.

The inoculum to be introduced into the growth tank described hereunder, was prepared as follows:
- a sample of monoalgal culture previously preserved at −85° C. in a 10% glycerine solution, was defrosted leaving it at room temperature, it was then subjected to centrifugation to remove the supernatant obtaining a cellular paste;
- the cellular paste thus obtained was inoculated into three 250 ml flasks containing 50 ml of solution comprising nutrients obtaining an algal culture;
- said algal culture was grown in a lighted climatic chamber at a constant temperature of 30° C., in the presence of 0.596 of $CO_2$ in air;
- after about a week, the flask reached a concentration of 0.3 g/l, this culture was used as inoculum for three 1 litre flasks containing 500 ml of solution comprising nutrients and placed in the climatic chamber;
- after 2 days the culture had a concentration of 0.5 g/l and this culture was used as inoculum for a laboratory growth tank having a volume of 35 litres.

The inoculum, prepared as described above, was grown in the culture medium M4N, described in literature for the cultivation of microalgae. The growth conditions were the following:
Water: drinkable;
$KNO_3$: 5.0 g/l;
$KH_2PO_4$: 1.25 g/l;
$CaCl_2$: 0.01 g/l;
$FeSO_4.7H_2O$: 0.003 g/l;
$MgSO_4.7H_2O$: 2.5 g/l;
Microelements: 1 ml/l of the following solution: 2.86 g of $H_3BO_3$, 1.81 g of $MnCl_2.4H_2O$, 80 mg of $CuSO_4.5H_2O$, 220 mg of $ZnSO_4.7H_2O$, 210 mg of $Na_2MoO_4$, 25 g of $FeSO_4.7H_2O$, 33.5 g of EDTA and 1 drop of concentrated $H_2SO_4$ per litre; operating pH: 7.8.

Inoculum tank: 10% by volume of the above culture in M4N medium.

The tank was illuminated from the outside by means of 17,500 Lux tungsten lamps and was maintained at 28° C. by means of thermostatic water circulation. The tank was also fed with a mixture of air and $CO_2$ at 10% in air, at a flow-rate of 200 litres/hour, under a pH control (pH set point 7.0).

Tank culture medium (optimized M4N):
Water: drinkable;
$KNO_3$: 1.5 g/l;
$KH_2PO_4$: 1.25 g/l;
$K_2HPO_4$: 0.1 g/l;
$CaCl_2$: 0.01 g/l;
$FeSO_4.7H_2O$: 0.003 g/l;
$MgSO_4O_4.7H_2O$: 1.5 g/l;
Microelements: 1 ml/l of the following solution: 2.86 g of $H_3BO_3$, 1.81 g of $MnCl_2.4H_2O$, 80 mg of $CuSO_4.5H_2O$, 220 mg of $ZnSO_4.7H_2O$, 210 mg of $Na_2MoO_4$, 25 g of $FeSO_4.7H_2O$, 33.5 g of EDTA and 1 drop of concentrated $H_2SO_4$ per litre;
operating pH: 7.0.

When shifts of ±0.2 units were noticed with respect to pH 7.0, the $CO_2$ flow was manually modified.

The composition above reported was obtained by modifying the typical culture medium M4N described in literature for the cultivation of microalgae. In particular, the modifications made are:
- reduction of the $KNO_3$ content from 5.0 g/l to 1.5 g/l;
- addition of $K_2HPO_4$ in an amount of 0.1 g/l;
- reduction in the content of $MgSO_4.7H_2O$ from 2.5 g/l to 1.5 g/l;
- reduction in the operating pH from 7.8 to 7.0.

Three samples of culture in a tank were taken and subjected to optical density measurements by means of a Varian C 900 spectrophotometer to be able to follow the algal growth trend.

In addition to this measurement, dry weight measurements were made to determine the effective concentration reached by the cultures. Table 1 summarizes the results obtained (triplicate values).

TABLE 1

|  | Optical density (750 nm) | | | | | | | | | Dry weight |
| --- | --- | --- | --- | --- | --- | --- | --- | --- | --- | --- |
| Time (hrs) | 0 | 3 | 5 | 20.5 | 24 | 29 | 44.5 | 48 | 52 | (g/l) |
|  | 0.415 | 0.500 | 0.570 | 1.550 | 1.840 | 2.200 | 2.850 | 3.180 | 3.350 | 0.835 |
|  | 0.670 | 0.760 | 0.830 | 1.500 | 1.550 | 1.720 | 2.300 | 2.410 | 2.540 | 0.925 |
|  | 0.510 | 0.570 | 0.620 | 1.330 | 1.250 | 1.460 | 1.900 | 1.980 | 2.060 | 0.580 |

The algal biomass obtained was centrifuged in a disk centrifuge of the Alfa Laval type obtaining an aqueous suspension of algal biomass having a volume of about 2 litres (concentration of dry substance 10 g/litre).

The aqueous suspension of algal biomass was then subjected to filtration under vacuum until a concentration of dry substance varying from 5% by weight to 10% by weight with respect to the total weight of the aqueous suspension of algal biomass, was obtained.

The samples obtained were preserved in a refrigerator before being subjected to hydrolysis and extraction of fatty acids.

EXAMPLE 2

Invention

Extraction of Fatty Acids (Concentration of Dry Substance Equal to 10%) and their Esterification for the Production of Methyl Esters (Biodiesel)

50 ml of n-octane and 0.5 ml of concentrated sulfuric acid at 96%, were added to a 250 ml three-necked flask, equipped with a reflux cooler and stirrer, containing 50 g of an aqueous suspension of algal biomass of algae of the strain *Scenedesmus* sp. obtained as described in Example 1, having a concentration of dry substance equal to 10% by weight with respect to the total weight of the aqueous suspension of algal biomass.

The flask was brought to the boiling point of water (100° C.) by means of a heating jacket. The reaction mixture was maintained, under stirring, at said temperature, for 2 hours.

During the hydrolysis/extraction, the formation of fatty acids was monitored by means of gas-chromatographic analysis of samples of the reaction mixture taken directly from the reaction flask at various times: the results obtained are reported in Table 2.

For this purpose, the samples taken at various times were subjected to rapid centrifugation in order to separate the solvent (n-octane) containing the fatty acids as they were formed in the reaction mixture. The samples of solvent thus obtained were analyzed using a Agilent mod 6890 gas chromatograph, equipped with a DB-5HT column 30 m long, having an internal diameter of 0.32 mm, and with a FID detector (flame-ionization detector), operating under the following conditions:

carrier gas: helium at 15 psi;
FID temperature detector: 400° C.;
temperature of the oven: 50° C. (starting); increase in temperature 10° C./min up to 400° C.; permanence at 400° C. for 12 min.

After 2 hours, the stirring was stopped, the mixture was brought back to room temperature and the three phases were left to separate by gravity.

The organic phase, about 50 ml, comprising n-octane, fatty acids and hydrophobic organic compounds different from said fatty acids, was recovered by taking it directly from the reaction flask and was placed in an ampoule equipped with a reflux cooler and stirrer.

20 ml of methanol and 1 ml of concentrated sulfuric acid at 96% as esterification catalyst of the fatty acids, were then added. The esterification reaction was carried out at 60° C., under stirring.

The formation of methyl esters was monitored by means of gas-chromatographic analysis at various times, operating under the same conditions described above: the results obtained are reported in Table 2.

TABLE 2

Gas-chromatography analysis results
(% with respect to the concentration of the initial dry substance)

| Reaction time (hrs) | Total fatty acids extracted | Total methyl esters (esterification fatty acids) |
|---|---|---|
| 0.5 | 4.5 | 4.2 |
| 1.0 | 5.5 | 5.4 |
| 1.5 | 6.3 | 6.0 |
| 2.0 | 6.3 | 6.5 |

EXAMPLE 3

Comparative

Extraction of Fatty Acids and Lipids (Concentration of Dry Substance Equal to 10%) and Transesterification of Said Lipids for the Production of Methyl Esters (Biodiesel)

A production test of methyl esters from lipids was effected as a control, using methods known in the art.

For this purpose, 50 g of an aqueous suspension of algal biomass from algae of the strain *Scenedesmus* sp. obtained as described in Example 1, having a concentration of dry substance equal to 10% by weight with respect to the total weight of the aqueous suspension of algal biomass, were subjected to mechanical lysis in a ball mill (Fritsch Pulverisette), operating at 500 of the maximum rate, for 20 minutes, then dried by lyophilization.

The lipid fraction was extracted from 5 g of algal biomass treated as described above with 150 ml of a chloroform/methanol mixture (1:2 v/v). After separation of the semisolid phase containing the slurry of the algal biomass by centrifugation, the methanol was eliminated from the organic phase by the addition of water and subsequent separation by demixing of the aqueous phase and part of the methanol contained therein.

An aliquot of this organic phase equal to 20 ml was placed in an ampoule equipped with a reflux cooler and stirrer. 1 ml of concentrated sulfuric acid at 96% was subsequently added.

The ampoule was brought to a temperature of 60° C. by means of a heating jacket. The reaction mixture was maintained, under stirring, at this temperature, for 2 hours.

After 2 hours, the stirring was stopped and the reaction mixture was brought back to room temperature. The amount of fatty acids formed was measured by means of gas-chromatographic analysis operating under the same conditions described above: the results are indicated in Table 3.

A second aliquot of said organic phase equal to 20 ml was introduced into an ampoule equipped with a reflux cooler and stirrer. 20 ml of methanol and 1 ml of concentrated sulfuric acid at 96% as transesterification catalyst, were subsequently added.

The ampoule was brought to a temperature of 60° C. by means of a heating jacket. The reaction mixture was maintained, under stirring, at this temperature for 2 hours.

After 2 hours, the stirring was stopped and the reaction mixture was brought back to room temperature. The amount of methyl esters formed was measured by means of gas-chromatographic analysis, operating under the same conditions described above: the results obtained are indicated in Table 3.

TABLE 3

Gas-chromatography analysis results
(% with respect to the concentration of the initial dry substance)

| Reaction time (hrs) | Total fatty acids extracted | Total methyl esters (lipid transesterification) |
|---|---|---|
| 2 | 6.3 | 6.5 |

Upon comparing Table 3 with Table 2, it can be observed that the process according to the present invention, although much simpler, has analogous yields to those obtained with the methods known in the art.

EXAMPLE 4

Invention

Extraction of Fatty Acids (Concentration of Dry Substance Equal to 5%)

50 ml of n-octane and 0.5 ml of concentrated sulfuric acid at 96% were added to a 250 ml three-necked flask, equipped with a reflux cooler and stirrer, containing 50 g of an aqueous suspension of algal biomass of algae of the strain *Scenedesmus* sp. obtained as described in Example 1, having a concentration of dry substance equal to 5% by weight with respect to the total weight of the aqueous suspension of algal biomass.

The flask was brought to the boiling point of water (100° C.) by means of a heating jacket. The reaction mixture was maintained, under stirring, at said temperature, for 2 hours.

After 2 hours, the stirring was stopped and the reaction mixture was brought back to room temperature. The amount of fatty acids formed was measured by means of gas-chromatographic analysis, operating under the same conditions described above: an amount of fatty acids equal to 6.3% was observed with respect to the concentration of initial dry substance.

EXAMPLE 5

Invention

Extraction of Fatty Acids (Concentration of Dry Substance Equal to 5%—different inorganic acid)

50 ml of n-octane and 1.0 ml of hydrochloric acid at 37% were added to a 250 ml three-necked flask, equipped with a reflux cooler and stirrer, containing 50 g of an aqueous suspension of algal biomass of algae of the strain *Scenedesmus* sp. obtained as described in Example 1, having a concentration of dry substance equal to 5% by weight with respect to the total weight of the aqueous suspension of algal biomass.

The flask was brought to the boiling point of water (100° C.) by means of a heating jacket. The reaction mixture was maintained, under stirring, at said temperature, for 2 hours.

After 2 hours, the stirring was stopped and the reaction mixture was brought back to room temperature. The amount of fatty acids formed was measured by means of gas-chromatographic analysis, operating under the same conditions described above: an amount of fatty acids equal to 6.6% was observed with respect to the concentration of initial dry substance.

EXAMPLE 6

Invention

Extraction of Fatty Acids (Concentration of Dry Substance Equal to 10%—Different Organic Solvent)

50 ml of hexane and 0.5 ml of concentrated sulfuric acid at 96% were added to a 250 ml three-necked flask, equipped with a reflux cooler and stirrer, containing 50 g of an aqueous suspension of algal biomass of algae of the strain *Scenedesmus* sp. obtained as described in Example 1, having a concentration of dry substance equal to 10% by weight with respect to the total weight of the aqueous suspension of algal biomass.

The flask was brought to the boiling point close to that of hexane (69° C.) by means of a heating jacket. The reaction mixture was maintained, under stirring, at said temperature, for 2 hours.

During the hydrolysis/extraction, the formation of fatty acids was monitored by means of gas-chromatographic analysis of samples of the reaction mixture taken directly from the reaction flask at various times, operating under the same conditions described above: the results obtained are indicated in Table 4.

TABLE 4

Gas chromatography analysis results
(% with respect to the concentration of the initial dry substance)

| Reaction time (hrs) | Total extracted fatty acids |
|---|---|
| 1.0 | 3.3 |
| 2.0 | 4.2 |
| 3.0 | 5.0 |
| 4.0 | 5.8 |

EXAMPLE 7

Invention

Quantification and Characterization of the Compounds Present in the Three Phases (i)-(iii)

300 ml of n-octane and 13 ml of hydrochloric acid at 37% were added to a 2-litre three-necked flask, equipped with a reflux cooler and stirrer, containing 630 g of an aqueous suspension of algal biomass of algae of the strain *Scenedesmus* sp. obtained as described in Example 1, having a concentration of dry substance equal to 5% by weight with respect to the total weight of the aqueous suspension of algal biomass.

The flask was brought to the boiling point of water (100° C.) by means of a heating jacket. The reaction mixture was maintained, under stirring, at said temperature, for 2 hours.

After 2 hours, the stirring was stopped and the reaction mixture was brought back to room temperature. The amount of fatty acids formed was measured by means of gas-chromatographic analysis, operating under the same conditions described above: an amount of fatty acids equal to 6.2% was observed with respect to the concentration of initial dry substance, and an amount of total lipids equal to 7.2% with respect to the concentration of initial dry substance.

The liquid phases: the aqueous phase (ii) and the organic phase (iii) were recovered by means of overflowing.

The solid phase (i) remaining in the flask was washed twice with about 160 ml of water each time. The washing water was removed by decanting the residual algal biomass and by subsequent overflowing.

The following materials were then recovered:
- semisolid phase (i): 90.2 g of slurry of the algal biomass with a concentration of dry substance of 12.5% by weight with respect to the total weight of the aqueous suspension of the algal biomass;
- aqueous phase (ii): 974 ml of aqueous phase also comprising the washing phase of the slurry of the algal biomass;
- organic phase (iii): 300 ml of organic phase having a content of fatty acids equal to 6.5 g/litre (6.2% by weight with respect to the concentration of initial dry substance).

The above materials were subjected to the analyses indicated in Table 5: the results obtained are indicated in Table 6.

TABLE 5

| | Analysis method |
|---|---|
| COD | Greenberg, Clescerl, Eaton, Standard Methods for the Examination of Water and Wastewater No. 5220, 18$^{th}$ Ed., Hanover Maryland, (1992) |
| Carbohydrates | Trevelyan and Harrison, Arch. Biochem. Biophys., 39(2): pg. 419-139 (1952) |
| Proteins | Bradford, Bio-rad Protein Assay Biochem 72, pg. 248 (1976) |

The amount of total lipids and the amount of fatty acids were measured by means of gas-chromatographic analysis operating under the same conditions described above: the results are indicated in Table 6.

TABLE 6

| | Algal biomass | | Weight % with respect to the aqueous suspension of the starting algal biomass | | |
|---|---|---|---|---|---|
| | | | Semisolid phase | Aqueous phase | Organic phase |
| | g/l (*) | g (**) | (i) | (ii) | (iii) |
| COD | 75.0 | 47.2 | 53.3 | 36.2 | 10.4 |
| Carbohydrates | 5.0 | 3.1 | 80.0 | 12.0 | 8.0 |
| Proteins | 32.0 | 20.3 | 40.0 | 58.5 | 1.5 |
| Total lipids | 11.0 | 6.9 | — | — | 32.8 |
| Fatty acids | 0.5 | 0.3 | — | — | 651 |

(*): g/l in the starting inoculum;
(**): g in the aqueous suspension of starting algal biomass

The invention claimed is:

1. A process for the extraction of fatty acids from algal biomass comprising:
   producing an aqueous suspension of algal biomass;
   subjecting the aqueous suspension of algal biomass to acid hydrolysis and extraction by adding at least one non-polar organic solvent and at least one inorganic acid to said aqueous suspension of algal biomass, so as to obtain the following three phases:
   (i) a semisolid phase comprising a slurry of the algal biomass;
   (ii) an aqueous phase comprising inorganic compounds and hydrophilic organic compounds;
   (iii) an organic phase comprising fatty acids and hydrophobic organic compounds other than said fatty acids.

2. The process according to claim 1, wherein the aqueous suspension of algal biomass derives from the cultivation of unicellular algae (microalgae), effected on wastewaters coming from an industrial wastewater.

3. The process according to claim 1, wherein the aqueous suspension of algal biomass is subjected to thickening in order to obtain a higher concentration of dry substance in said algal biomass.

4. The process according to claim 1, wherein the aqueous suspension of algal biomass has a concentration of dry substance ranging from 3% by weight to 40% by weight with respect to the total weight of the aqueous suspension of algal biomass.

5. The process according to claim 4, wherein the aqueous suspension of algal biomass has a concentration of dry substance ranging from 5% by weight to 35% by weight with respect to the total weight of the aqueous suspension of algal biomass.

6. The process according to claim 1, wherein the at least one non-polar organic solvent is selected from the group consisting of an aliphatic hydrocarbon; an aromatic hydrocarbon; a refinery cut which comprises an aliphatic hydrocarbon, an aromatic hydrocarbon or a mixture of aliphatic and aromatic hydrocarbons; and a petroleum ether.

7. The process according to claim 6, wherein the at least one non-polar organic solvent is a aliphatic hydrocarbon selected from the group consisting of hexane, and n-octane.

8. The process according to claim 4, wherein the ratio between the concentration of dry substance in the algal biomass and the volume of the at least one non-polar organic solvent ranges from 1:1 to 1:80.

9. The process according to claim 8, wherein the ratio between the concentration of dry substance in the algal biomass and the volume of the at least one non-polar organic solvent ranges from 1:3 to 1:70.

10. The process according to claim 1, wherein the at least one inorganic acid is selected from the group consisting of sulfuric acid, hydrochloric acid, phosphoric acid, and nitric acid.

11. The process according to claim 10, wherein the at least one inorganic acid is selected from the group consisting of sulfuric acid, hydrochloric acid, and phosphoric acid.

12. The process according to claim 4, wherein the ratio between the concentration of dry substance in the algal biomass and the volume of the at least one inorganic acid ranges from 1:0.01 to 1:5.

13. The process according to claim 12, wherein the ratio between the concentration of dry substance in the algal biomass and the volume of the at least one inorganic acid ranges from 1:0.02 to 1:3.

14. The process according to claim 1, wherein the acid hydrolysis and extraction are carried out, at atmospheric pressure and at a temperature of the boiling point of the at least one non-polar organic solvent, if said temperature is lower than 100° C.

15. The process according to claim 1, wherein the acid hydrolysis and extraction are carried out, at atmospheric pressure and at 100° C., if the boiling point of the at least one non-polar organic solvent is higher than 100° C.

16. The process according to claim 1, wherein the acid hydrolysis and extraction are carried out, at atmospheric pressure and at 100° C.

17. The process according to claim 1, wherein the acid hydrolysis and extraction are carried out at a temperature of 100° C. and at an equilibrium pressure of the at least one non-polar organic solvent at said temperature.

18. The process according to claim 1, wherein the acid hydrolysis and extraction are carried out at a pH ranging from 0.5 to 3.

19. The process according to claim 18, wherein the acid hydrolysis and extraction are carried out at pH 2.

20. The process according to claim 1, wherein the acid hydrolysis and extraction are carried out for a time ranging from 1 hour to 3 hours.

21. The process according to claim 20, wherein the acid hydrolysis and extraction are carried out for 2 hours.

22. The process according to claim 1, wherein the at least one non-polar organic solvent and the at least one inorganic acid are added contemporaneously to the algal biomass.

23. The process according to claim 1, wherein the at least one non-polar organic solvent is added to the algal biomass before the at least one inorganic acid.

24. The process according to claim 1, wherein the at least one non-polar organic solvent is added to the algal biomass after the at least one inorganic acid.

25. The process according to claim 1, wherein the semi-solid phase (i) comprising a slurry of the algal biomass, after removing the residual water, is subjected to pyrolysis in order to obtain a pyrolytic oil.

26. The process according to claim 1, wherein the aqueous phase (ii) comprising inorganic compounds and hydrophilic organic compounds is subjected to anaerobic digestion with a microorganism in the absence of oxygen in order to obtain a biogas.

27. The process according to claim 1, wherein phase (i) and phase (ii) are mixed and subsequently subjected to anaerobic digestion with a microorganism in the absence of oxygen in order to obtain biogas.

28. The process according to claim 26 or 27, wherein the at least one non-polar organic solvent is hydrochloric acid.

29. The process according to claim 1, wherein the organic phase (iii) comprising fatty acids and other hydrophobic organic compounds other than said fatty acids is subjected to evaporation in order to recover the at least one non-polar organic solvent which is recycled to the process.

30. The process according to claim 29, wherein said organic phase (iii) is subjected to esterification in the presence of an alcohol having from 1 to 4 carbon atoms and an acid or basic catalyst, in order to produce glycerol and alkyl esters.

31. The process according to claim 29, wherein said organic phase (iii) is subjected to hydrogenation/deoxygenation in the presence of hydrogen and a catalyst in order to produce green diesel.

32. The process according to claim 1, wherein the organic phase (iii) comprising fatty acids and other hydrophobic organic compounds other than said fatty acids is subjected directly to esterification, or hydrogenation/deoxygenation.

* * * * *